(12) United States Patent
Satheesan et al.

(10) Patent No.: US 6,934,356 B1
(45) Date of Patent: Aug. 23, 2005

(54) SYSTEM AND METHOD FOR DYNAMIC GENERATION OF A SINGLE USER INTERFACE FOR DISPLAYING AND ENTRY OF MEDICAL IMAGING CONFIGURATION DATA

(75) Inventors: Sajith Satheesan, Mahararshtra (IN); Medhi O. Venon, Whitefish Bay, WI (US)

(73) Assignee: General Electric Company, Schenectady, NY (US)

( * ) Notice: Subject to any disclaimer, the term of this patent is extended or adjusted under 35 U.S.C. 154(b) by 1 day.

(21) Appl. No.: 10/604,448

(22) Filed: Jul. 22, 2003

(51) Int. Cl.[7] .............................................. A61B 6/03
(52) U.S. Cl. .............................. 378/62; 378/4; 378/901
(58) Field of Search ........................... 378/4, 8, 15, 19, 378/62, 901

(56) References Cited

U.S. PATENT DOCUMENTS

| 5,390,335 | A | 2/1995 | Stephan et al. |
| 5,793,368 | A | 8/1998 | Beer |
| 2002/0196293 | A1 | 12/2002 | Suppan et al. |
| 2003/0046548 | A1 | 3/2003 | Brown et al. |
| 2003/0051039 | A1 | 3/2003 | Brown et al. |
| 2003/0061567 | A1 | 3/2003 | Brown et al. |

FOREIGN PATENT DOCUMENTS

| GB | 2363872 | 1/2002 |
| JP | 2001-184327 | 7/2001 |
| WO | WO 98/21642 | 5/1998 |

*Primary Examiner*—David V Bruce
(74) *Attorney, Agent, or Firm*—Ziolkowski Patent Solutions Group, SC; Michael A. Della Penn; Carl B. Horton (57) ABSTRACT

A system and method for dynamically generating an interface includes a hierarchical organization data file defining a hierarchical organization of subsystems of a medical imaging scanner and at least one parsing component to extract configuration parameter names from the data file and generate a graphical representation of the hierarchical organization of the medical imaging scanner. A configuration servlet extracts configuration parameters of the medical imaging scanner, associates the configuration parameters with the graphical representation of the hierarchical organization, and displays the configuration parameters and graphical representation of the organization in a single user interface such that the configuration parameters can be reviewed and edited in the single user interface.

45 Claims, 4 Drawing Sheets

SYSTEM AND METHOD FOR DYNAMIC GENERATION OF A SINGLE USER INTERFACE FOR DISPLAYING AND ENTRY OF MEDICAL IMAGING CONFIGURATION DATA

BACKGROUND OF INVENTION

The present invention relates generally to medical imaging systems, and more particularly, to a system for dynamic generation of a single interface for a medical imaging scanner to allow a user to review and edit configuration parameters of the medical imaging scanner from the single web-based interface.

Medical imaging scanning devices, such as computer tomography (CT) systems, x-ray systems, magnetic resonance imaging (MRI) systems, positron emission tomography (PET) systems and the like, are defined by a number of subsystems that control the major functionalities of the device. For example, some subsystems of an x-ray scanner include an x-ray generator, a table positioner, a system control, and an operator console. These subsystems may be further subdivided into subsystems of the subsystem, or micro-subsystems. For example, the operator console may include multiple control interfaces such as keyboards, mice, and touch-screen monitors wherein each has multiple outputs or inputs or multiple functions and therefore is considered an individual subsystem of the operator console subsystem and has specific software dedicated to interpreting user input therefrom. This amalgamation of subsystems results in a distributed overall system hardware configuration. Due to this distributed configuration, the overall x-ray scanner functionality is commonly achieved using distributed object oriented infrastructure components as a middleware interface between the specific software running the various scanner subsystems or between the subsystems and external user applications.

One type middleware implementation that is commonly selected in medical imaging scanners is Common Object Request Broker Architecture (CORBA®). CORBA® is a registered trademark of Object Management Group, Inc., of Farmingham, Mass. A CORBA® architecture is a platform-independent architecture that facilitates the interaction of computer applications that are not readily capable of interaction. A program based on the CORBA® architecture will be able to communicate with other applications regardless of computer manufacturer, operating system, programming language, and network. CORBA® applications are composed of "objects" or individual units of software that can be combined to develop functionality. An "object" is generally defined as a programming component that can be used to build arrangements of variables and operations therein. Applications built with this "object-oriented" programming are developed in a block-by-block or "object-by-object" fashion. These arrangements can be logically grouped into "structures" or "classes." Each "class" can be designed to perform a specific operation or operations on data passed to it by another class.

Typically, in object-oriented programming, each object includes an "interface." The "interface" for each object is the syntax of the object that allows other objects to invoke the object. A first object that wishes to invoke an operation by a second object uses the interface to "call" the second object, and pass on the arguments on which the operation must be performed. When the operation is complete, the interface is then used to collect the results for forwarding to the desired destination; typically, back to the first object that requested the operation.

The distributed object oriented infrastructure components provide a means whereby the interface definition is independent of programming language. Independence is achieved by mapping the interface to multiple programming languages such as C, C++, and Java®. Java® is a registered trademark of Sun Microsystems, Inc., of Palo Alto, Calif. This separation of the interface and the execution is a chief benefit of implementing distributed object oriented infrastructure components. In a medical imaging device, distributed object oriented infrastructure components are used to enable the interaction of the various subsystems of the medical imaging device. As such, the distributed object oriented infrastructure components need to access configuration data necessary for the proper running of the subsystem. This configuration data is stored in configuration files which are initially defined and used during the running of the system. During the servicing of such an x-ray system, a service engineer uses an interface to access the configuration data. Should the engineer or other service technician need to change or otherwise update the configuration data, the engineer must use a second and separate application that provides a second and separate user interface specifically designed to facilitate editing of the configuration data. That is, a second user interface is required for the user to change the configuration parameters and communicate those changes to a distributed object oriented infrastructure component for implementation.

For example, a service engineer, when servicing a scanner, must first review the data in one user interface and then switch to a separate user interface to edit the data. This requirement of a second and separate user interface to permit the service engineer to change configuration data creates a servicing and/or maintenance process that is arduous, time consuming, and error prone.

The process of changing the configuration data can be arduous because the service must switch repeatedly between the "viewing" interface and the "editing" interface. Furthermore, by requiring a separate user interface for editing configuration data, the service engineer is effectively tethered to the system. That is, while the "viewing" interface is typically displayable in a web browser and therefore, can easily be made accessible remotely, the "editing" interface is not as readily accessible from remote locations. That is, while the "viewing" web browser interface is readily compliant with internet compatibility standards, the "editing" interface is not necessarily compliant with those standards. Therefore, the service engineer is effectively tethered by the "editing" interface to a local proximity of the medical imaging device being serviced.

Additionally, the process of changing the configuration data is susceptible to error because the imposition of a second and separate interface for editing configuration parameters raises the probability of human error. For example, the service engineer is more likely to enter erroneous configurations or enter the correct configuration in an incorrect area when switching from the review interface to the separate edit interface. Errors in configuration data can cause the medical imaging device being serviced to operate improperly or not at all. In such a case, a second servicing is typically required to remedy the configuration error. These repetitive service calls can be extremely costly in both time and resources. In addition, the servicing downtime for the medical imaging scanner can be an impediment to the efficient and effective practice of medicine.

It would therefore be desirable to have a system and method capable of dynamically generating a single user interface for display and entry of medical imaging configuration parameters.

BRIEF DESCRIPTION OF INVENTION

The present invention provides a system and method of dynamically generating a single user interface for the display and entry of medical imaging configuration parameters that overcomes the aforementioned drawbacks. Specifically, the invention is directed to a system to gather the necessary configuration parameters from various subsystems of a medical imaging system and dynamically generate a single web-based user interface that displays the configuration parameters and allows the parameters to be edited.

In accordance with one aspect of the invention, a system of dynamically generating an interface is disclosed that has a hierarchical organizational data file defining a hierarchical organization of subsystems of a medical imaging device and at least one parsing component to extract configuration parameter names from the data file and generate a graphical representation of the hierarchical organization of the medical imaging device. A configuration servlet is provided to extract configuration parameters of the medical imaging device, associate the configuration parameters with the graphical representation of the hierarchical organization, and display the configuration parameters and graphical representation of the organization in a single user interface wherein the configuration parameters can be reviewed and edited in the single user interface.

In accordance with another aspect of the invention, a method of dynamically generating an interface is disclosed that includes defining a hierarchical organization of subsystems of a medical imaging device in a hierarchical organization data file, extracting configuration parameter names from the data file, and extracting configuration parameters of the medical imaging device. The method further includes generating a graphical representation of the hierarchical organization of the medical imaging device, associating the configuration parameters with the graphical representation of the hierarchical organization, and displaying the configuration parameters and the graphical representation of the hierarchical organization in a single user interface. In this regard, the configuration parameters can be reviewed and edited in the single user interface.

In accordance with yet another aspect of the invention, a medical imaging scanner is disclosed that includes a plurality of subsystems as well as a computer programmed to define a hierarchical organization of subsystems of a medical imaging device in a hierarchical organization data file wherein sections map to subsystems of the medical imaging scanner and subsections map to sub-subsections of the medical imaging scanner. The computer is also programmed to extract configuration parameter names from the data file, extract configuration parameters of the medical imaging device, and generate a graphical representation of the hierarchical organization of the medical imaging device. The computer then associates the configuration parameters with the graphical representation of the hierarchical organization and displays the configuration parameters and the graphical representation of the hierarchical organization in a single user interface thereby allowing the configuration parameters to be reviewed and edited in the single user interface.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

The present invention is operable with a wide variety of medical imaging systems and devices. As will be described in detail below, the present invention is not hardware specific and, therefore, readily portable and adaptable for operation with various medical imaging systems. As will be further described, the claimed invention is operable with middleware interfaces regardless of the specific hardware or software of the underlying system. Specifically, the current invention is operable with a wide range of medical imaging systems that can be defined by subsystems and subsystems within the subsystems, or micro-subsystems, that readily map to middleware interfaces. However, a single system component can make or be a subsystem, as that term is used herein. Such systems are defined to include any imaging system, including computer tomography (CT) systems, x-ray systems, magnetic resonance imaging (MRI) systems, ultrasound systems, positron emission tomography (PET) systems, and the like.

Figure 1:
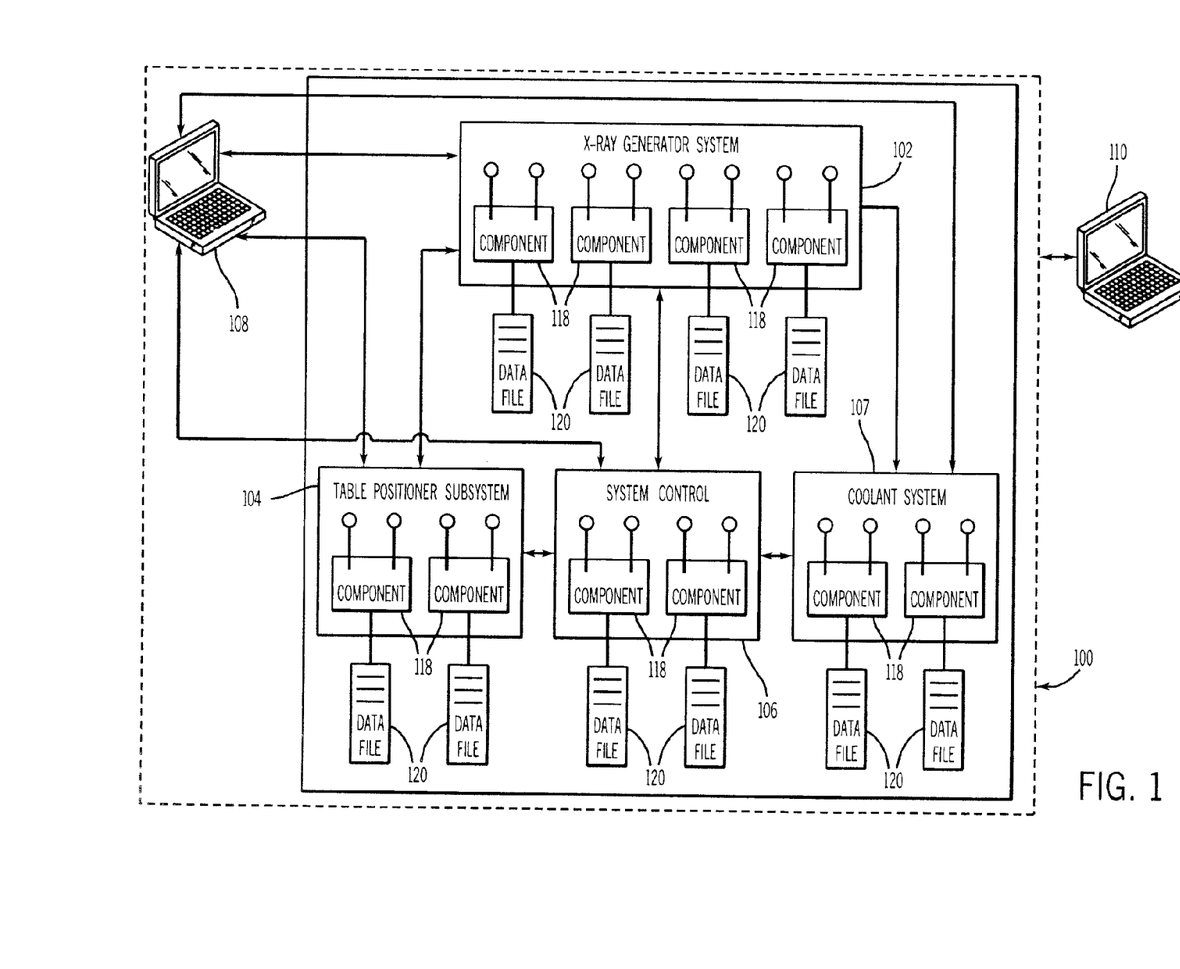
FIG. 1 is a block schematic diagram of a medical imaging system in accordance with one embodiment of the present invention.

FIG. 1 is a graphical representation of examples of various subsystems of a medical imaging scanner. An x-ray scanner 100 is shown, including an x-ray generator subsystem 102, a table positioner subsystem 104, a system control subsystem 106, a subsystem coolant system 107, and an operator console subsystem 108. Though only specific subsystems are shown, it should be understood that the current invention contemplates any number of subsystems. Furthermore, these subsystems may be defined by further subsystems or micro-systems. For example, the operator console 108 may have multiple control interfaces such as a keyboard, mouse, buttons, touch screen monitor, switches, and dials. Each control interface is a further subsystem or micro-system of the operator console subsystem 108. This amalgamation of subsystems results in a distributed overall system hardware and software configuration. Due to this distributed configuration, medical imaging scanner functionality is commonly achieved using distributed object oriented infrastructure components as a middleware interface between the specific software running on the various scanner subsystems or between the subsystems and external user applications.

The service computer 110, capable of generating a user interface, communicates with the x-ray scanner 100. Through a process that will be described in detail below, the information necessary to generate the user interface on the service computer 110 is gathered from the subsystems 102, 104, 106, 107, 108 of the x-ray scanner 100. Corresponding to each subsystem 102, 104, 106, 107, 108 is at least one distributed object computing infrastructure component 118. In a preferred embodiment, the distributed object computing infrastructure component 118 is a CORBA® component.

The component 118, when contacted by the service computer 110, extracts the desired configuration parameters from data files 120 and passes the configuration parameters to the service computer 110.

Therefore, FIG. 1 shows several subsystems from which the necessary information to generate a user interface is gathered. As will be shown, the configuration parameters are organized in a user interface into sections and subsections such that subsystems of the medical imaging scanner are displayed as sections of the user interface and further subsystems of the subsystem, or micro-subsystems, are displayed as subsections.

Figure 2:
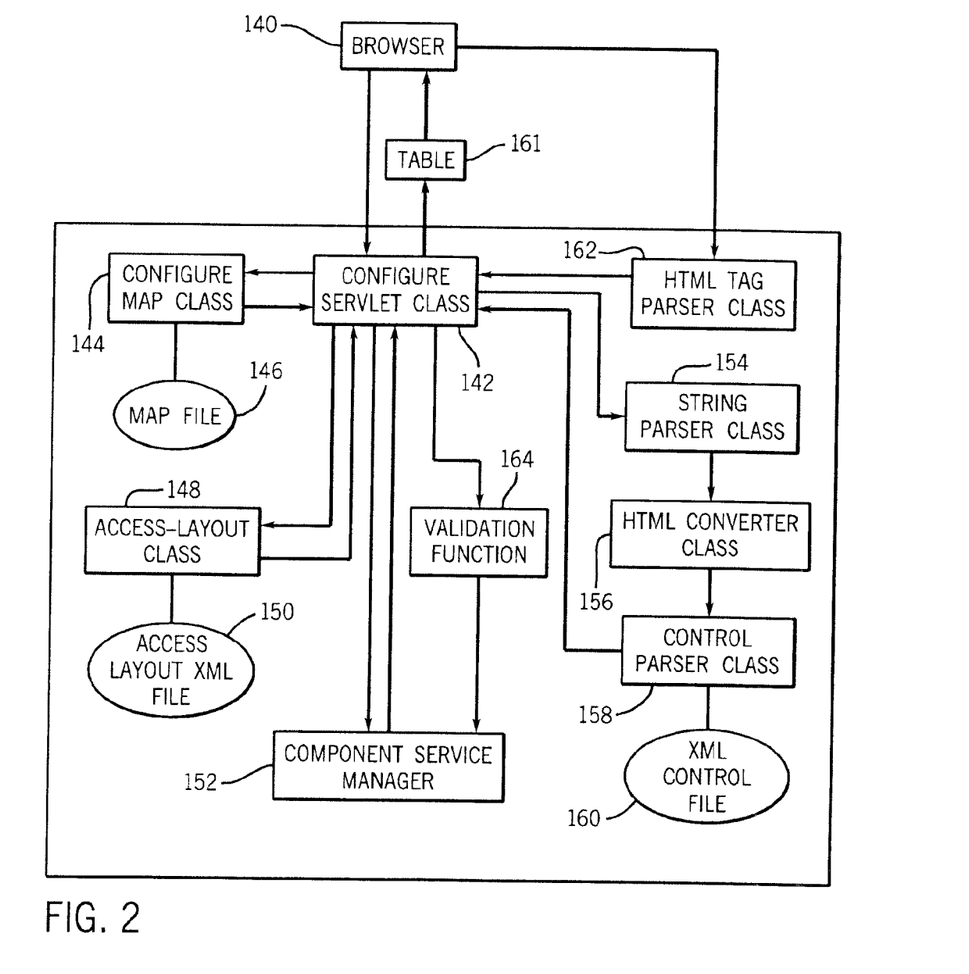
FIG. 2 is a graphic representation of software components used to dynamically create a user interface in accordance with one embodiment of the present invention.

Referring now to FIG. 2, examples of components used to extract and generate the user interface are shown. When a user initiates the generation of the user interface via browser 140, a configuration servlet 142 passes a configuration parameter name that will be displayed to configuration map class 144. The configuration map class 144 then locates a distributed object computing infrastructure component name associated with the requested configuration parameter name in a configuration map file 146 and returns the distributed object computing infrastructure component name configuration servlet 142.

The configuration servlet 142 then passes the configuration parameter name to an access-layout class 148. In response, the access-layout class 148 retrieves layout information associated with the configuration parameter from an access-layout extensible markup language (XML) file 150. After receipt of layout information the configuration servlet 142 creates an organizational table for the later generated Hypertext Markup Language (HTML) code. Then the configuration servlet 142 makes a call to a component service manager 152 to request the desired configuration parameter value.

The main parameters passed to the component service manager 152 include section name, configuration parameter name, and the distributed object computing infrastructure component name associated with the configuration parameter name. The service manager 152 retrieves the requested configuration parameters and, through the configuration servlet 142, sends a string representation value to a string parser class 154, which extracts the actual data and stores it in private variables. The data is read from a "point-of-view" file which is organized in a hierarchical manner that will correspond to the hierarchical manner of displaying the sections and subsections within the user interface. The string parser 154 then calls an HTML converter class 156. In turn, the HTML converter class 156 converts the necessary HTML and calls a control parser class 158. The control parser class 158 extracts controls from a XML control file 160 and combines the data with HTML tags passed by the HTML converter class 156 to generate an HTML output according to the hierarchical organization in sections and subsections corresponding to the subsystems of the medical imaging system being accessed. Furthermore, the XML control file 160 sets forth the particular manner in which the configuration parameter will be displayed in the user interface. Specifically, the XML control file 160 sets forth the manner in which each of data type of the configuration parameter. As such, different visual representations of the same data are possible within the structure of the single user interface.

Upon receipt of the HTML output at the configuration servlet 142, the configuration servlet 142 places the HTML output in the correct row and column of a table 161 generated by the configuration servlet 142. The table 161 is then passed to and displayed in a user interface within the user's web browser 140 in the desired hierarchical organization and with the desired number of rows and columns for the data. As such, the user is able to review the configuration parameters through the single user interface.

After review of the configuration parameters, the user may conclude that changes to the configuration parameters are necessary. Upon submission of a change to the configuration parameters, the currently displayed values, including the user changes, are passed to an HTML tag parser class 162. The HTML tag parser class 162 parses the values into the specific configuration parameters and passes them to the configuration servlet 142. The configuration servlet 142 then passes the changes to a verification function 164 to verify the validity of the submitted change. Numerous validation functions 164 are possible, each of which is named by the configuration servlet 142 at run time. The configuration servlet 142 uses the configuration parameter names to generate the validation function names. Thus, the number of validation functions 164 defined is dependent upon the number of configuration parameters present in the medical imaging scanner. After validation, the submitted change is passed to the component service manager 152 to implement the submitted change. Therefore, through the single user interface, the service engineer can review, edit and update any configuration parameters of the medical imaging scanner.

Included in the access-layout class 144 is support for access control of various user profiles. Along with retrieving layout information associated with the configuration parameter from an access-layout XML file 150, the access-layout class retrieves access information. The information is also stored in the map file 146. Specifically, the access information is stored as an access rights string. Each value stored in the map file 146 has a corresponding access rights string. As such, when the organizational table is generated by the configuration server 142, a determination is made for each table entry as to whether the current user has access rights to change and/or view each entry. Furthermore, since each entry in the map file 146 has its own access rights string associated with it, each access rights determination is made independently.

Figure 3:
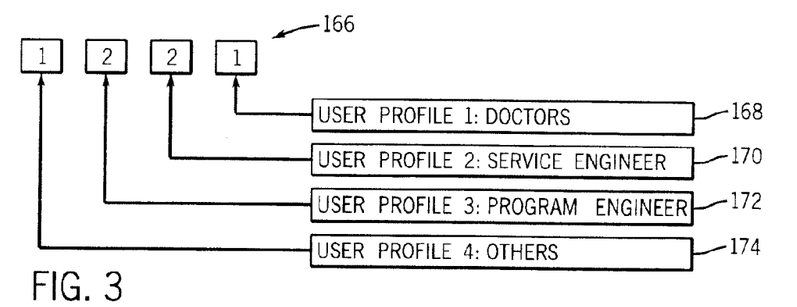
FIG. 3 is a graphic representation of an implementation of access rights management in accordance with one embodiment of the present invention.

Referring now to FIG. 3, a graphical representation of an example of an access rights string and corresponding profiles are shown. In the given example, "1", "2", "2", and "1" represents the access rights string 166. The position in the access rights string 166 indicates the user profile under consideration. The actual value of the digit indicates the type of access allowed. Typically, a value of "1" indicates that the specific value associated with the access rights string is read-only for the given user profile and a value of "2" indicates that the value is read-write for the given profile. In such a case, a value of "3" indicates that the associated value is hidden from the view for the given profile. In this preferred embodiment, FIG. 3 shows that for: (1) User Profile 1: Doctors 168 have read-only access for the associated value; (2) User Profile 2: Service Engineers 170 have read-write access for the associated value; (3) User Profile 3: Program Engineers 172 have read-write access for the associated value; and (4) User Profile 4: any Others 174 that have access will have read-only access for the associated value.

Figure 4:
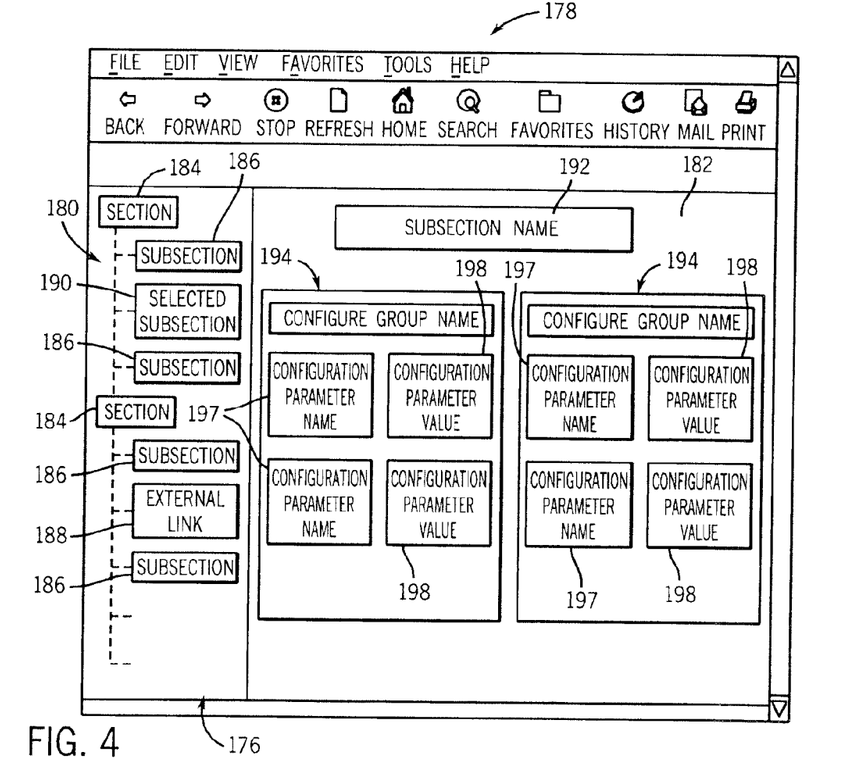
FIG. 4 is a representation of a graphical user interface in accordance with one embodiment of the present invention.

Referring now to FIG. 4, a graphical representation of a user interface 176 is generated when accessing the medical imaging scanner for configuration review and editing. The interface 176 is shown displayed in a web browser 178 and complies with common internet protocol standards so that it may be readily accessed either locally or remotely. The interface 176 is further broken down into a hierarchical organization section 180, which is a graphical representation of the subsystems of the medical imaging scanner, and configuration parameter display section 182, which displays the desired data. The hierarchical organization section 180 shows sections 184 and subsections 186 that correspond to the subsystems of the medical imaging scanner. Additionally, hypertext transfer protocol (http) links 188 to information located externally from the medical imaging scanner, or external links 188, can be provided as an additional resource for the user, which when selected causes the interface to seamlessly display the external information.

Upon selecting a subsection 190, the configuration parameter display section 182 is updated to display the data that is specific to the selected subsection 190. A section or subsection name 192 is displayed indicating the subsystem of the medical imaging scanner to which the displayed information pertains. Certain sections or subsections may necessitate the display of multiple configuration parameters. As such, the configuration parameter display section 182 can be further broken into configuration groups 194. In this regard, a configuration group name 196 is displayed. Within each configuration group 194 configuration parameter names 197 and corresponding configuration parameter values 198 are displayed. Examples of configuration parameters include current value, voltage value, table position, screen brightness, and the like. Configuration parameters can be represented in several formats such as string, list of strings, number, list of numbers, floating-point numbers, matrix, and the like. Furthermore, the configuration parameters can be displayed in various formats. For example, a string data type can be displayed as a textbox, a part of a pull down list, a group of selection buttons, and the like. Since the nature of this data is dynamic, the mechanism for generation of subsection name, group name, configuration parameter, as well as the specific means of displaying the values, are also dynamic.

Additionally, a user, after reviewing the configuration parameters in the user interface 176, can update all or a portion of the values and then submit the changes. The changes made can be of various types, such as changing text in a textbox, selecting a different button in a group, selecting a different option in a pull down list, or checking a different checkbox in a list. In any case, the changes are implemented and configuration parameters are updated. Therefore, by gathering and organizing the configuration parameters of a medical imaging scanner, a user can access the single, dynamic, user interface 176 containing the data necessary to configure and maintain the medical imaging scanner. Furthermore, the user may edit the current configuration parameters of the medical imaging scanner within the single user interface 176 either locally or remotely.

Also, a group of configuration parameters falling within a particular subsection can be arranged in a number of fashions depending on the user interface requirements. Should the user or designer desire to show all configuration parameters at once, without the need for scrolling within the window, the user can specify that the data be organized in a specific number of rows and columns. On the other hand, if the user or designer desires a simpler display, the user can specify that the data be displayed in a single column. As previously shown with respect to FIG. 2, a layout table is used when generating the user interface that may contain any variation of rows and columns to organize the display as necessary.

Similarly, as previously shown with respect to FIG. 3, there may be multiple users that require varying levels of access to the information displayed by the user interface. In this case, the user interface includes profiles, whereby some users have the right to modify the data while other users may only review the data or part of the data. Specifically, an access control mechanism is included that shows the configuration parameter values as read-write, read-only, or hidden depending upon the user profile of the user accessing the data.

Figure 5:
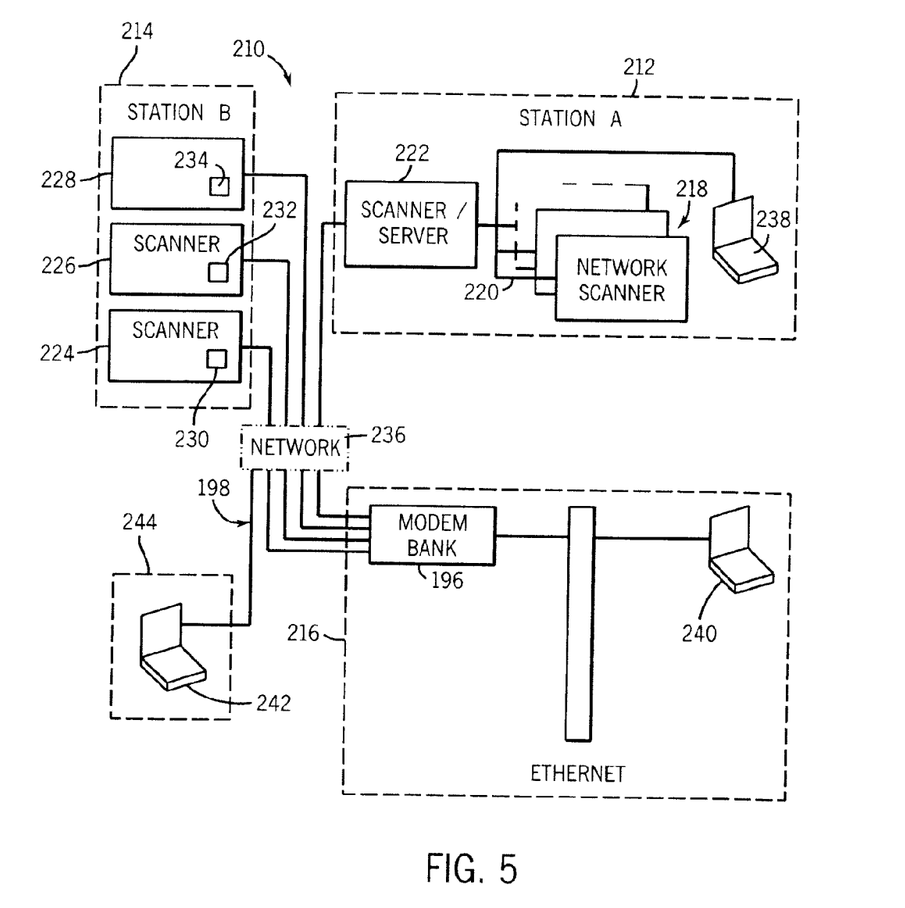
FIG. 5 is a schematic representation of a multi-node network of medical imaging systems.

Referring now to FIG. 5, an overview block diagram of a medical diagnostic and service networked system 210 is shown which includes a plurality of treatment stations or nodes, such as Station A 212, and Station B 214, which may include a medical treatment facility, hospital, clinic, or mobile imaging facility. The treatment stations 212, 214 may be connected to a centralized facility 216 through a communications link, such as a network of interconnected server nodes. Each treatment station has operational software associated therewith which can be configured, serviced, maintained, upgraded, monitored, and enabled or disabled locally at the station or from the centralized facility 216.

In general, a treatment site may have a number of devices such as a variety of medical diagnostic systems of various modalities. As another example, in the present embodiment, the devices in a treatment station, such as that shown with reference to treatment station 212, may include a number of networked medical image scanners 218 connected to an internal network 220 served by a single scanner 222 having a workstation configured to also act as a server, or configured as a stand-alone server without a medical image scanner associated therewith. Alternately, a treatment station or treatment site 214 can include a number of non-networked medical image scanners 224, 226, and 228 each having a computer or workstation associated therewith. Each scanner may be of the same modality or be of different modality. Any imaging scanner modality is contemplated. In the case of treatment station 214, an internal modem 230, 232, 234 may be included to connect the remote treatment station to a communications link 236 to allow communication between the treatment stations 212, 214 and a centralized facility 216. The communications link 236 is shown in phantom to indicate that it may include an external public or semi-public communications network, such as the internet, or may be a more secure dedicated communications link or intranet.

The embodiment shown in FIG. 5 contemplates a medical facility having such systems as MRI systems, ultrasound systems, x-ray systems, CT systems, as well as PET systems, or any other type of medical imaging system, however, the present invention is not so limited to any particular imaging system. Such facilities may also provide services to centralized medical diagnostic management systems, picture archiving and communications systems (PACS), teleradiology systems, etc.

As stated, these medical imaging systems regularly require setup, configuration, servicing, and maintenance. Service engineers and other users access configuration interfaces either through a workstation integrated within the treatment station 212, 214 through a portable service/configuration computer 238 that can be carried to the treatment station 212, 214, through a workstation 240 in a remote service station 216 or through a mobile workstation 242 in a mobile service station 244 when servicing the medical imaging scanner 218, 224, 226, 228. The service computer 238, 240, 242 is enabled to display the user interface of the present invention to enable the user to access and change system configuration parameters of the medical imaging scanner 218, 224, 226, 228 through an interface.

Through this architecture and technique it is possible to dynamically generate a single interface for a medical imaging scanner to allow a user to review and edit configuration parameters of the medical imaging scanner from the single interface. The invention overcomes the limitations present when requiring multiple review and edit interfaces. Furthermore, the technique facilitates remote servicing while providing specific checks against erroneous configurations and unapproved access.

The invention described above is highly portable, highly customizable, and may be adapted to operate with a wide variety of medical imaging products regardless of modality. Specifically, because the invention is not operating environment dependent, it may be integrated into multiple systems regardless of operating system or hardware configuration. The invention provides a means of easily updating the web-based user interface to display various visual representations and styles within the user interface. Furthermore, the current invention provides high layout flexibility by placing the configuration parameters in a table. As such, the above described invention is highly flexible such that it may be adapted to meet the needs and preferences of a wide variety of systems and users.

It is contemplated that the above architecture and technique can be embodied in any modality of medical imaging scanner or within a portable servicing device such that, when accessed by a user, the medical imaging scanner or portable servicing device is caused to implement the above process.

It is further contemplated that the above architecture and technique can be embodied in a computer program, stored on a computer readable storage medium, and executable by a local or remote computer. The program, when executed by one or more processors of a computer system and/or server, causes the computer system and server to implement the above process.

The present invention has been described in terms of the preferred embodiments, and it is recognized that equivalents, alternatives, and modifications, aside from those expressly stated, are possible and within the scope of the appending claims.

What is claimed is:

1. A system of dynamically generating an interface comprising:
   a hierarchical organization data file defining a hierarchical organization of each subsystem of a medical imaging device;
   at least one parsing component to extract configuration parameter names from the data file and generate a graphical representation of the hierarchical organization of the medical imaging device; and
   a configuration servlet to extract configuration parameters of the medical imaging device and associate the configuration parameters with the graphical representation of the hierarchical organization and display the configuration parameters and graphical representation of the organization in a single user interface, wherein the configuration parameters can be reviewed and edited in the single user interface.

2. The system of claim 1 further comprising a layout information data file to map the configuration parameters to user defined layout preferences.

3. The system of claim 2 wherein the at least one parsing component is configured to parse the layout information data file into rows and columns corresponding to the configuration parameters.

4. The system of claim 2 wherein the configuration servlet displays the graphical representation of the configuration parameters according to the user defined layout preferences.

5. The system of claim 1 further comprising an access rights data file defining specific configuration parameters that a current user is permitted to view wherein the at least one parsing component parses the access rights data file and the configuration servlet displays the graphical representation of the configuration parameters according to the access rights data file.

6. The system of claim 5 wherein the configuration parameters are hidden if the current user is not permitted to view specific configuration parameters.

7. The system of claim 1 wherein the hierarchical organization data file further defines data to generate links to data that is external from the medical imaging device.

8. The system of claim 1 wherein the configuration parameters are extracted from distributed object computing infrastructure components.

9. The system of claim 1 wherein the single user interface is a web-based interface capable of being displayed in a web browser.

10. The system of claim 1 wherein the configuration servlet extracts the configuration parameters by requesting the configuration parameter names.

11. The system of claim 10 wherein the configuration servlet extracts the configuration parameters by requesting the configuration parameters from distributed object computing infrastructure components that store the configuration parameters.

12. The system of claim 11 wherein multiple graphical representations for each configuration parameter is selectable.

13. The system of claim 1 further comprising an XML control file setting forth each of a plurality of data types to a manner of displaying each of the data types.

14. The system of claim 1 wherein the at least one parsing component is an XML parsing component.

15. The system of claim 14 wherein the at least one parsing component is further configured to extract HTML tags from the layout data file and wherein the configuration servlet is further configured to replace a section of the HTML tag with the configuration parameters to display the configuration parameters and the graphical representation of the configuration parameters in the manner specified by an XML control file.

16. The system of claim 1 further comprising a validation tool to dynamically validate user input into the user interface, wherein the validation tool includes a number of validation functions and wherein the configuration servlet assigns names to the number of validation functions.

17. The system of claim 16 wherein the user input into the user interface is validated based upon the validation function names.

18. The system of claim 16 wherein the configuration servlet assigns names to the number of validation functions at a startup of the medical imaging device.

19. The system of claim 16 wherein the number of number of names the configuration servlet assigns to the number of validation functions is dependent upon the number of configuration parameters.

20. The system of claim 16 wherein information for generating the validation function names is stored in the hierarchical organization data file.

21. The system of claim 16 wherein the at least one parsing component extracts the information for generating the validation function names from the hierarchical organization data file.

22. A method of dynamically generating an interface comprising:
   defining a hierarchical organization of subsystems of a medical imaging device in a hierarchical organization data file;
   extracting configuration parameter names from the hierarchical organization data file;
   extracting configuration parameters of the medical imaging device;
   generating a graphical representation of the hierarchical organization of the medical imaging device;
   associating the configuration parameters with the graphical representation of the hierarchical organization; and
   displaying the configuration parameters and the graphical representation of the hierarchical organization in a single user interface wherein the configuration parameters can be reviewed and edited in the single user interface.

23. The method of claim 22 further comprising:
   mapping configuration parameter layout data from the configuration parameters to user defined layout preferences; and
   storing the configuration parameter layout data in the hierarchical organization data file.

24. The method of claim 23 wherein the displaying of the configuration parameters is based on an XML control file and the graphical representation of the hierarchical organization is based on the layout information data file.

25. The method of claim 22 further comprising:
   defining specific configuration parameters that a current user is permitted to view; and
   storing the specific configuration parameters that a current user is permitted to view in an access rights data file and displaying the configuration parameters and the graphical representation of the hierarchical organization according to the access rights data file.

26. The method of claim 22 further comprising displaying links to data that is external from the medical imaging device as links in the single user interface so that a user can review additional information stored externally from the medical imaging system.

27. The method of claim 22 wherein the configuration parameters are extracted from distributed object computing infrastructure components.

28. A medical imaging scanner comprising:
   a plurality of subsystems to execute one or more imaging applications; and
   a computer programmed to:
   define a hierarchical organization of the subsystems of a medical imaging scanner in a hierarchical organization data file, wherein sections map to the subsystems, and subsections map to further micro-subsystems;
   extract configuration parameter names from the hierarchical organization data file;
   extract configuration parameters of the medical imaging scanner;
   generate a graphical representation of the hierarchical organization of the medical imaging scanner;
   associate the configuration parameters with the graphical representation of the hierarchical organization; and
   display the configuration parameters and the graphical representation of the hierarchical organization in a single user interface wherein the configuration parameters can be reviewed and edited in the single user interface.

29. The medical imaging scanner of claim 28 wherein the computer is further programmed to:
   map a configuration parameter layout data from the configuration parameters to user defined layout preferences;
   parse the layout data file into rows and columns corresponding to the configurations parameters; and
   store the configuration parameter layout data in a hierarchical organization data file.

30. The medical imaging scanner of claim 29 wherein computer is further programmed to:
   extract HTML tags from the layout data file; and
   replace a section of the HTML tag with the configuration parameters to display the configuration parameters and the graphical representation of the configuration parameters in the manner specified by an XML control file.

31. The medical imaging scanner of claim 29 wherein computer is further programmed to display of the configuration parameters and the graphical representation of the hierarchical organization is based on the layout data file.

32. The medical imaging scanner of claim 28 wherein the computer is further programmed to define specific configuration parameters that a current user is permitted to view.

33. The medical imaging scanner of claim 28 wherein computer is further programmed to store the specific configuration parameters that a current user is permitted to view in an access rights data file and display the configuration parameters and the graphical representation of the hierarchical organization according to the access rights data file and hide the configuration parameters from display if the current user is not permitted to view specific configuration parameters.

34. The medical imaging scanner of claim 28 wherein computer is further programmed to display links to data that is external from the medical imaging system as HTTP links in the single user interface so that a user can review additional information stored externally from the medical imaging system.

35. The medical imaging scanner of claim 28 wherein the computer is further programmed to extract the configuration parameters from distributed object computing infrastructure components.

36. The medical imaging scanner of claim 28 wherein the single user interface is a web-based interface capable of being displayed in a web browser.

37. The medical imaging scanner of claim 28 wherein the computer is further programmed to dynamically validate user input into the single user interface.

38. The medical imaging scanner of claim 37 wherein the user input into the user interface is validated based upon the configuration parameter names.

39. A computer readable storage medium having stored thereon a computer program comprising instructions which, when executed by at least one processor, cause the at least one processor to:
   define a hierarchical organization data file wherein subsystems of a medical imaging scanner map to sections and micro-systems map to subsections of the medical imaging scanner;
   extract configuration parameters of the medical imaging scanner from the medical imaging scanner;
   generate a graphical representation of the hierarchical organization of the medical imaging scanner;
   associate the configuration parameters with the graphical representation of the hierarchical organization; and display the configuration parameters and the graphical representation of the hierarchical organization in a single user interface wherein the configuration parameters can be reviewed and edited in the single user interface.

40. The computer readable storage medium of claim 39 wherein the at least one processor is further caused to:

map configuration parameter layout data from the configuration parameters to user defined layout preferences; and store the configuration parameter layout data in the hierarchical organization data file.

41. The computer readable storage medium of claim 39 wherein displaying the configuration parameters and the graphical representation of the hierarchical organization is based on the layout information data file.

42. The computer readable storage medium of claim 39 wherein the at least one processor is further caused to display links to data that is external from the medical imaging system as HTTP links in the single user interface so that a user can review additional information stored externally from the medical imaging system.

43. The computer readable storage medium of claim 39 wherein the configuration parameters are extracted from distributed object computing infrastructure components.

44. The computer readable storage medium of claim 39 wherein the at least one processor is further caused to dynamically validate user input into the user interface.

45. The computer readable storage medium of claim 44 wherein the user input into the user interface is validated based upon configuration parameter names.

* * * * *